United States Patent [19]

Kutsher et al.

[11] Patent Number: 4,581,154
[45] Date of Patent: Apr. 8, 1986

[54] SOLVENT COMPOSITION FOR THE REMOVAL OF ACID GAS FROM GAS MIXTURES AT SUBFREEZING TEMPERATURES

[75] Inventors: George S. Kutsher, Dover; John P. Valentine, Belle Mead, both of N.J.

[73] Assignee: Norton Company, Worcester, Mass.

[21] Appl. No.: 725,877

[22] Filed: Apr. 22, 1985

Related U.S. Application Data

[63] Continuation of Ser. No. 562,898, Dec. 19, 1983.

[51] Int. Cl.$^4$ .......................... C11D 7/50; B01D 53/34
[52] U.S. Cl. ..................................... 252/170; 252/70; 252/71; 252/73; 252/364; 55/73
[58] Field of Search ................... 252/364, 170, 70, 71, 252/73; 55/73; 568/613

[56] References Cited

U.S. PATENT DOCUMENTS

| | | | |
|---|---|---|---|
| 3,362,133 | 1/1968 | Kutsher et al. | 55/44 |
| 3,503,186 | 3/1970 | Ward | 55/16 |
| 3,653,183 | 4/1972 | Sanders et al. | 55/56 |
| 3,737,392 | 6/1973 | Ameen et al. | 252/364 |
| 3,972,949 | 8/1976 | Arpe | 260/615 R |
| 4,302,220 | 11/1981 | Volkamer et al. | 55/32 |

*Primary Examiner*—Paul Lieberman
*Assistant Examiner*—Hoa Van Le
*Attorney, Agent, or Firm*—Frank S. Chow

[57] ABSTRACT

A new solvent comprising a mixture of dialkyl ethers of polyalkylene glycols of the formula: $CH_3O(C_2H_4O)_x CH_3$ wherein x is 3 to 8 and having a molecular weight of 200 to 255 is disclosed. This solvent system is particularly suitable for use in removing acidic components from gas mixtures in subfreezing temperatures.

4 Claims, No Drawings

SOLVENT COMPOSITION FOR THE REMOVAL OF ACID GAS FROM GAS MIXTURES AT SUBFREEZING TEMPERATURES

This application is a continuation of application Ser. No. 562,898, filed Dec. 19, 1983.

BACKGROUND OF THE INVENTION

The present invention relates to a composition of matter and more particularly it relates to a mixture of dialkyl ethers of polyalkylene glycols useful in removing acidic gas components such as hydrogen sulfide from gas mixtures. Still more particularly the present invention relates to a mixture of dimethyl ethers of polyethylene glycol, having an average molecular weight of from about 200 to 255, and preferably from 227 to 244, which is effective at low temperatures for the removal of acidic gas components from gas mixtures.

U.S. Pat. No. 3,737,392 teaches that a certain mixture of dimethyl ethers of polyethylene glycols is useful in treating and separating acid gas particularly hydrogen sulfide from gas mixtures such as natural gas mixtures containing hydrogen sulfide, carbon dioxide and methane. Such a solvent system available under the trademark SELEXOL has been widely and successfully used in many natural gas treating operations.

However, it has been found that such a solvent system does not operate efficiently at subfreezing temperatures. Thus, for example, at about 10° F. to about −10° F. the solvent rapidly becomes rather viscous. The increased viscosity tends to reduce the rate of solvent flow through a gas absorber so that less and less gas can be treated. Further at this low temperature the solvent starts to freeze, fouling heat exchangers. Then mass transfer problems begin to appear further reducing the efficiency of the gas treating operation. The solvent according to the present invention markedly alleviates and in some instances completely eliminates these problems.

SUMMARY OF THE INVENTION

The improved solvent composition according to the present invention comprises a mixture of dimethyl ethers of polyethylene glycols of the formula:

$$CH_3O(C_2H_4O)_xCH_3 \qquad (I)$$

wherein x is from about 3 to about 8. The homolog distribution (I) is approximately as follows:

|  Homolog distribution, $CH_3(C_2H_4O)_x CH_3$ | |  |
|---|---|---|
| x | Molecular homolog wt. % | |
| 2 | about | 0.1–1 |
| 3 | about | 8–50 |
| 4 | about | 28–40 |
| 5 | about | 7–33 |
| 6 | about | 2–24 |
| 7 | about | 0–5 |
| 8 | about | 0–2 |

A preferred homolog distribution is approximately as follows:

| $CH_3O(C_2H_4O)_x CH_3$ (II) | | |
|---|---|---|
| x | Molecular homolog wt. % | |
| 2 | about | 0.1–0.5 |
| 3 | about | 12–22 |
| 4 | about | 30–36 |
| 5 | about | 28–33 |
| 6 | about | 8–12 |
| 7 | about | 2–7 |
| 8 | about | 0.1–1.0 |

The above solvent composition II has a vapor pressure of about 0.0003 mm of Hg and a viscosity of about 11 centipoises at a temperature of about 15° F. (−9.4° C.) and a vapor pressure of about 0.0001 mm of Hg and a viscosity of about 18 centipoises at a temperature of about 0° F. (−18° C.).

The solvent composition may be used in known processes for separating hydrogen sulfide, carbon dioxide and mercaptans from gases, and it is particularly suitable in a subfreezing environment. As an example, the instant solvent composition may be used in place of the solvent SELEXOL disclosed and described in the aforementioned U.S. Pat. No. 3,737,392. The disclosure in the U.S. Pat. No. 3,737,392 for treating gases is accordingly incorporated herein by reference. Another example would be the process disclosed in U.S. Pat. No. 3,362,133.

DESCRIPTION OF PREFERRED EMBODIMENT

The mixture of dimethyl ethers of polyethylene glycols of the present invention is prepared from the corresponding monomethyl ethers of polyethylene glycols by reacting the monomethyl ether, with sodium to form the sodium alcoholate thereof, reacting the sodium alcoholate with methyl chloride to form the dimethyl ethers and sodium chloride, and separating the sodium chloride from the dimethyl ethers. Preferably, about 0.1–0.6 weight percent of water is incorporated in the monomethyl ethers, and the reaction temperature is maintained at about 100°–120° C.

The mixture of monomethyl ethers of polyethylene glycols from which the diethers are derived may be prepared from ethylene oxide and methanol. About 4.5 mols of ethylene oxide is reacted with 1 mol of methanol at about 110°–140° C. using sodium hydroxide as catalyst. The resulting product is distilled at about 10 mm. Hg pressure to remove all of the low-boiling compounds, together with most of the monomethyl ether of triethylene glycol.

The most preferred solvent composition has the following approximate homolog distribution:

| Homolog distribution, $CH_3O(C_2H_4O)_x CH_3$ (III) | |
|---|---|
| x | Molecular homolog, wt. % |
| 2 | 0.5 |
| 3 | 17.0 |
| 4 | 33.0 |
| 5 | 33.0 |
| 6 | 10.5 |
| 7 | 5.0 |
| 8 | 1 |
| m.wt = | 237.0 |

An example of the important physical properties of the most preferred solvent composition III are listed below:

| | |
|---|---|
| Vapor pressure, 15° F., mm Hg | 0.0003 |
| Viscosity, 15° F., cp | 11 |
| Viscosity, 50° F., cp | 5.5 |
| Viscosity, 90° F., cp | 3.3 |
| Specific heat, 41° F., | 0.46 |
| Freezing point, °F., | −20 to −36 |
| Pounds per gallon, 77° F., | 8.5 |
| Flash point, °F., (COC) | 300 |

It is of course understood that in the above formulations (I, II or III), minor amounts of lower and higher homologs may be tolerated so long as the physical properties which will permit the solvent to be efficient at sub-freezing temperatures e.g. viscosity are not affected.

A preferred process for removing acid gas from a gas mixture containing acidic components e.g. carbon dioxide, hydrogen sulfide and mercaptans may be practiced according to the following steps:

(a) contacting said gaseous mixture in a first absorption zone under superatmospheric pressure with a solvent comprising a mixture of dimethyl ethers of polyethylene glycols according to II or III above preferably having dissolved therein at least 1 weight percent acid gas to effect absorption of most of the acid gas so as to partially purify the gas;

(b) contacting said partially purified gas from the first absorption zone in a second absorption zone under superatmospheric pressure with the same solvent containing less than 1 weight percent acid gas to produce a purified gas;

(c) passing the solvent containing dissolved gases from the second absorption zone to the first absorption zone;

(d) passing the solvent containing dissolved acid gas from the first absorption zone to a flashing zone maintained at a pressure substantially lower than that in the first absorption zone to effect liberation of most of the acid gas therefrom;

(e) withdrawing from said flashing zone gases liberated therein;

(f) passing a major portion of solvent containing at least 1 weight percent acid gas from said flashing zone to said first absorption zone;

(g) passing a minor portion of solvent containing at least 1 weight percent acid gas from said flashing zone to a stripping zone;

(h) stripping substantially all of the acid gas from said minor portion of solvent; and (i) returning desorbed solvent to the second absorption zone for further contact with the gaseous mixture.

The invention will be described further in conjunction with the following examples which are not intended to be limitative in nature.

EXAMPLE I

Preparation of a mixture of monomethyl ethers of polethylene glycols

A carbon steel reactor equipped with a central agitator and means for heating and cooling was charged with 7 lbs. of 50 weight percent aqueous sodium hydroxide and 865 pounds of methanol. The mixture was heated to 110° C., and 4757 pounds of ethylene oxide was added to the mixture over a period of several hours. Reaction temperature was maintained at 110°–140° C. by cooling. The pressure remained below 150 p.s.i.a. The resulting mixture was then cooled to 60° C. and stored. This crude product had an average molecular weight of 204 and contained monomethyl ethers of mono-through octaethylene glycols.

The crude product was batch distilled in a 4 plate column operating at a pressure of 10 mm, Hg and a reflux ratio of 1. Lights were removed until the overhead temperature of the column reached about 155° C. The column bottoms were taken as product and had the following composition:

| Monomethyl ether of: | Weight percent |
|---|---|
| Triethylene glycol | 17 |
| Tetraethylene glycol | 33 |
| Pentaethylene | 33 |
| Hexaethylene glycol | 11 |
| Heptaethylene glycol | 5 |
| Octaethylene glycol | 1 |

Average molecular weight of this mixture of monomethyl ethers of polyethylene glycols was about 224.

EXAMPLE II

Preparation of a mixture of dimethyl ethers of polyethylene glycols

A stainless steel reactor equipped with means for agitating, heating, and cooling was charged with 1080 lbs. of monomethyl ethers of polyethylene glycols prepared in Example I and having an average molecular weight of about 224. About 4.6 lbs. of water was added and the mixture was agitated and heated to 110° C. About 112 pounds of molten sodium at 135°–140° C., was added to the mixture over a period of several hours while the mixture was maintained at about 120°–130° C., by cooling. Hydrogen formed during the reaction was vented. The reaction yielded the sodium alcoholate of the monomethyl ethers of polyethylene glycol.

Next 305 pounds of methyl chloride was added to the reaction mixture over a period of several hours while the reaction mixture was maintained at about 115°–125° C. by cooling. The resulting reaction yielded sodium chloride and the dimethyl ethers of polyethylene glycols. The sodium chloride was separated from the reaction mixture in a centrifuge, and the resulting liquid product was stripped with natural gas to remove any excess methyl chloride. The stripped product was filtered, allowed to stand 24 hours and refiltered to remove any residual sodium chloride. This product may be distilled, if desired, but distillation is not necessary. The undistilled product had the following composition and an average molecular weight of 237:

| Dimethyl ether of: | Weight percent |
|---|---|
| Triethylene glycol | 17 |
| Tetraethylene glycol | 33 |
| Pentaethylene glycol | 33 |
| Hexaethylene glycol | 11 |
| Heptaethylene glycol | 5 |
| Octaethylene glycol | 1 |
| Water | 1 |

The properties of the undistilled, filtered product are shown below:

| | Filtered product |
|---|---|
| $CO_2$ solubility wt. percent; | |

| | Filtered product |
|---|---|
| At 215 p.s.i.a. partial pressure at 70° F. | 9.8 |
| At 900 p.s.i.a. partial pressure at 70° F. | 19.3 |
| H2S solubility, wt. percent: | |
| At 39 p.s.i.a. partial pressure at 70° F. | 8.7 |
| At 70 p.s.i.a. partial pressure at 70° F. | 15.6 |
| Chlorides p.p.m. | 8 |
| Viscosity, centipoises at 82° F. | 3.7 |
| Density, lbs/gal. at 82° F. | 8.5 |

EXAMPLE III

Preparation of a low molecular weight mixture of the dimethyl ethers of polyethylene glycol A vacuum distillation boiler is charged with 1005 lbs. of the dimethyl ethers of polyethylene glycol prepared in Example II. The 10-plate column was operated at 10 mm Hg and a reflux ratio of 1. Overhead product was condensed and collected until the overhead temperature reached 170° C. About 1005 lbs. of condensed product was collected and the composition was as follows:

| Dimethyl ether of: | Wt. percent |
|---|---|
| Diethylene glycol | 1 |
| Triethylene glycol | 51 |
| Tetraethylene glycol | 45 |
| Pentaethylene glycol | 3 |
| Hexaethylene glycol | — |
| Heptaethylene glycol | — |
| Octaethylene glycol | — |

Solubilities of carbon dioxide and hydrogen sulfide in the distilled product were similar to those of the higher molecular weight, undistilled product.

We claim:

1. A process for separating at least one acid gas from a mixture of at least one acid gas with at least one other gas, comprising:
    (a) contacting said gaseous mixture at a subfreezing temperature in an absorption zone under superatmospheric pressure with a solvent comprising a mixture of dimethyl ethers of polyethylene glycols of the formula $CH_3O(C_2H_4O)_xCH_3$, wherein x is an integer, to effect absorption of most of the acid gas so as to partially purify the gaseous mixture;
    (b) passing the solvent containing absorbed acid gas from the absorption zone to a flashing zone maintained at a pressure substantially lower than that in the first absorption zone to effect liberation of most of the acid gas therefrom;
    (c) withdrawing from said flashing zone the gases liberated therein; and,
    (d) returning desorbed solvent to the absorption zone for further contact with the gaseous mixture,
the improvement wherein the molecular homolog distribution of said mixture of dimethyl ethers of polyethylene glycols in terms of x is:

| Value of x | Molecular Homolog weight percent |
|---|---|
| 2 | 0.1–1 |
| 3 | 8–50 |
| 4 | 28–40 |
| 5 | 7–33 |
| 6 | 2–24 |
| 7 | 0–5 |
| 8 | 0–2. |

2. An improved process according to claim 1, wherein the the molecular homolog distribution of said mixture of dimethyl ethers of polyethylene glycols in terms of x is:

| Value of x | Molecular Homolog weight percent |
|---|---|
| 2 | 0.5 |
| 3 | 17 |
| 4 | 33 |
| 5 | 33 |
| 6 | 10.5 |
| 7 | 5.0 |
| 8 | 1. |

3. A process for separating at least one acid gas from a mixture of at least one acid gas with at least one other gas, comprising:
    (a) contacting said gaseous mixture at a subfreezing temperature in a first absorption zone under superatmospheric pressure with a solvent comprising a mixture of dimethyl ethers of polyethylene glycols of the formula $CH_3O(C_2H_4O)_xCH_3$, wherein x is an integer, to effect absorption of most of the acid gas so as to partially purify the gaseous mixture;
    (b) contacting said partially purified gaseous mixture from the first absorption zone in a second absorption zone under superatmospheric pressure with the same solvent containing less than 1% acid gas to produce a purified gas mixture;
    (c) passing the solvent containing dissolved acid gas from the second absorption zone to the first absorption zone;
    (d) passing the solvent containing dissolved acid gas from the first absorption zone to a flashing zone maintained at a pressure substantially lower than that in the first absorption zone to effect liberation of most of the acid gas therefrom;
    (e) withdrawing from said flashing zone any gases liberated therein;
    (f) passing a major portion of solvent containing at least 1 weight percent acid gas from said flashing zone to said first absorption zone;
    (g) passing a minor portion of solvent containing at least 1 weight percent acid gas from said flashing zone to a stripping zone;
    (h) stripping substantially all of the acid gas from said minor portion of solvent; and
    (i) returning desorbed solvent to the second absorption zone for further contact with the gaseous mixture, the improvement wherein the molecular homolog distribution of said mixture of dimethyl ethers of polyethylene glycols in terms of x is:

| Value of x | Molecular Homolog weight percent |
|---|---|
| 2 | 0.1–1 |
| 3 | 8–50 |
| 4 | 28–40 |
| 5 | 7–33 |
| 6 | 2–24 |
| 7 | 0–5 |
| 8 | 0–2. |

4. An improved process according to claim 3, wherein the the molecular homolog distribution of said mixture of dimethyl ethers of polyethylene glycols in terms of x is:

| Value of x | Molecular Homolog weight percent |
|---|---|
| 2 | 0.5 |
| 3 | 17 |
| 4 | 33 |
| 5 | 33 |
| 6 | 10.5 |
| 7 | 5.0 |
| 8 | 1. |

* * * * *